(12) United States Patent
Howell et al.

(10) Patent No.: US 7,993,329 B2
(45) Date of Patent: Aug. 9, 2011

(54) ERCP CATHETER WITH A REMOVABLE HANDLE FOR LITHOTRIPTOR COMPATIBLE BASKET

(75) Inventors: Douglas A. Howell, Cape Elizabeth, ME (US); Matthew P. Carter, Dobson, NC (US); Jason D. Foushee, Durham, NC (US); David M. Hardin, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1372 days.

(21) Appl. No.: 10/640,490

(22) Filed: Aug. 13, 2003

(65) Prior Publication Data
US 2004/0111082 A1     Jun. 10, 2004

Related U.S. Application Data

(60) Provisional application No. 60/403,123, filed on Aug. 13, 2002.

(51) Int. Cl.
*A61B 17/22* (2006.01)
(52) U.S. Cl. .......................... 606/2.5; 606/127; 606/128
(58) Field of Classification Search .................. 606/127, 606/128, 200, 2.5
See application file for complete search history.

(56) References Cited

U.S. PATENT DOCUMENTS

| 1,612,697 | A | 12/1926 | Cecil |
| 1,677,671 | A | 7/1928 | Councill |
| 2,711,734 | A | 6/1955 | Moe |
| 2,816,552 | A | 12/1957 | Hoffman |
| 2,918,919 | A | 12/1959 | Wallace |
| 3,043,309 | A | 7/1962 | McCarthy |
| 3,320,957 | A | 5/1967 | Sokolik |
| 3,472,230 | A | 10/1969 | Fogarty |
| 3,561,445 | A | 2/1971 | Katerndahl et al. |
| 3,592,186 | A | 7/1971 | Oster |
| 3,631,848 | A | 1/1972 | Muller |
| 3,674,033 | A | 7/1972 | Powers |
| 3,683,904 | A | 8/1972 | Forster |
| 3,683,928 | A | 8/1972 | Kuntz |
| 3,774,605 | A | 11/1973 | Jewett |
| 3,811,449 | A | 5/1974 | Gravlee et al. |
| 3,826,256 | A | 7/1974 | Smith |
| 3,835,854 | A | 9/1974 | Jewett |
| 3,838,688 | A | 10/1974 | May et al. |

(Continued)

FOREIGN PATENT DOCUMENTS

DE    3343231 A1 *   6/1985

(Continued)

OTHER PUBLICATIONS

Communication pursuant to Article 94(3) EPC dated May 16, 2008 for corresponding European Application No. 03 785 225.8.

*Primary Examiner* — Todd E Manahan
*Assistant Examiner* — Michael G Mendoza
(74) *Attorney, Agent, or Firm* — Brinks Hofer Gilson & Lione (57) ABSTRACT

An ERCP catheter having a removable handle for a lithotriptor compatible basket is disclosed. The removable handle allows the catheter and handle assembly to be removed, leaving the basket in place within the duct and facilitates the use of a lithotriptor for mechanically crushing stone captured in the basket.

5 Claims, 8 Drawing Sheets

U.S. PATENT DOCUMENTS

| | | |
|---|---|---|
| 3,952,747 A | 4/1976 | Kimmell, Jr. |
| 3,995,628 A | 12/1976 | Gula et al. |
| 3,996,938 A | 12/1976 | Clark, III |
| 4,046,150 A | 9/1977 | Schwartz et al. |
| 4,160,451 A | 7/1979 | Chittenden |
| 4,210,863 A | 7/1980 | Hunt et al. |
| 4,243,033 A | 1/1981 | DeCaprio et al. |
| 4,342,313 A | 8/1982 | Chittenden |
| 4,344,435 A | 8/1982 | Aubin |
| 4,397,091 A | 8/1983 | Gustavsson et al. |
| 4,401,433 A | 8/1983 | Luther |
| 4,425,908 A * | 1/1984 | Simon .......................... 128/899 |
| 4,435,853 A | 3/1984 | Blom et al. |
| 4,466,443 A | 8/1984 | Utsugi |
| 4,554,929 A | 11/1985 | Samson et al. |
| 4,573,470 A | 3/1986 | Samson et al. |
| 4,590,938 A | 5/1986 | Segura et al. |
| 4,592,341 A | 6/1986 | Omagari et al. |
| 4,616,653 A | 10/1986 | Samson et al. |
| 4,637,404 A | 1/1987 | Gessman |
| 4,641,654 A | 2/1987 | Samson et al. |
| 4,646,747 A | 3/1987 | Lundback |
| 4,650,466 A | 3/1987 | Luther |
| 4,655,750 A | 4/1987 | Vailancourt |
| 4,662,885 A | 5/1987 | DiPisa, Jr. |
| 4,664,113 A | 5/1987 | Frisbie et al. |
| 4,705,517 A | 11/1987 | DiPisa, Jr. |
| 4,706,671 A | 11/1987 | Weinrib |
| 4,713,059 A | 12/1987 | Bickelhaupt et al. |
| 4,723,549 A | 2/1988 | Wholey et al. |
| 4,741,335 A * | 5/1988 | Okada .......................... 606/127 |
| 4,748,982 A | 6/1988 | Horzewski et al. |
| 4,748,984 A | 6/1988 | Patel |
| 4,768,505 A | 9/1988 | Okada et al. |
| 4,790,812 A | 12/1988 | Hawkins, Jr. et al. |
| 4,791,913 A | 12/1988 | Maloney |
| 4,794,928 A | 1/1989 | Kletschka |
| 4,799,495 A | 1/1989 | Hawkins et al. |
| 4,807,626 A | 2/1989 | McGirr |
| 4,808,164 A | 2/1989 | Hess |
| 4,820,271 A | 4/1989 | Deutsch |
| 4,838,269 A | 6/1989 | Robinson et al. |
| 4,844,092 A | 7/1989 | Rydell et al. |
| 4,846,174 A | 7/1989 | Willard et al. |
| 4,852,568 A | 8/1989 | Kensey |
| 4,860,742 A | 8/1989 | Park et al. |
| 4,860,757 A | 8/1989 | Lynch et al. |
| 4,873,978 A | 10/1989 | Ginsburg |
| 4,903,826 A | 2/1990 | Pearce |
| 4,917,094 A | 4/1990 | Lynch et al. |
| 4,921,478 A | 5/1990 | Solano et al. |
| 4,921,484 A | 5/1990 | Hillstead |
| 4,926,858 A | 5/1990 | Gifford, III et al. |
| 4,944,740 A | 7/1990 | Buchbinder et al. |
| 4,957,117 A | 9/1990 | Wysham |
| 4,960,411 A | 10/1990 | Buchbinder |
| 4,966,583 A | 10/1990 | Debbas |
| 4,969,891 A | 11/1990 | Gewertz |
| 4,976,697 A | 12/1990 | Walder et al. |
| 4,986,279 A | 1/1991 | O'Neill |
| 4,996,583 A | 2/1991 | Hatada |
| 4,998,539 A | 3/1991 | Delsanti |
| 5,002,560 A | 3/1991 | Machold et al. |
| 5,011,488 A | 4/1991 | Ginsburg |
| 5,031,634 A | 7/1991 | Simon |
| 5,045,061 A | 9/1991 | Seifert et al. |
| 5,053,008 A | 10/1991 | Bajaj |
| 5,059,197 A | 10/1991 | Urie et al. |
| 5,064,415 A | 11/1991 | Walder et al. |
| 5,071,407 A | 12/1991 | Termin et al. |
| 5,098,441 A | 3/1992 | Wechler |
| 5,100,381 A | 3/1992 | Burns |
| 5,102,415 A | 4/1992 | Guenther et al. |
| 5,108,419 A | 4/1992 | Reger et al. |
| 5,114,414 A | 5/1992 | Buchbinder |
| 5,117,831 A | 6/1992 | Jang et al. |
| 5,117,838 A | 6/1992 | Palmer et al. |
| 5,117,839 A | 6/1992 | Dance |
| 5,125,416 A | 6/1992 | Phillips |
| 5,125,906 A | 6/1992 | Fleck |
| 5,133,364 A | 7/1992 | Palermo et al. |
| 5,133,733 A | 7/1992 | Rasmussen et al. |
| 5,137,288 A | 8/1992 | Starkey et al. |
| 5,152,777 A | 10/1992 | Goldberg et al. |
| 5,154,725 A | 10/1992 | Leopold |
| 5,158,548 A | 10/1992 | Lau et al. |
| 5,158,565 A | 10/1992 | Marcadis et al. |
| 5,163,927 A | 11/1992 | Woker et al. |
| 5,171,233 A | 12/1992 | Amplatz et al. |
| 5,183,463 A | 2/1993 | Debbas |
| 5,185,004 A | 2/1993 | Lashinski |
| 5,192,295 A | 3/1993 | Danforth et al. |
| 5,195,533 A | 3/1993 | Chin et al. |
| 5,209,730 A | 5/1993 | Sullivan |
| 5,217,435 A | 6/1993 | Kring |
| 5,219,332 A | 6/1993 | Nelson et al. |
| 5,221,269 A | 6/1993 | Miller et al. |
| 5,236,424 A | 8/1993 | Imran |
| 5,243,996 A | 9/1993 | Hall |
| 5,255,960 A | 10/1993 | Keith et al. |
| 5,267,982 A | 12/1993 | Sylvanowicz |
| 5,279,573 A | 1/1994 | Klosterman |
| 5,281,203 A | 1/1994 | Ressemann |
| 5,282,478 A | 2/1994 | Fleischhaker, Jr. et al. |
| 5,297,346 A | 3/1994 | Weiner |
| 5,311,858 A | 5/1994 | Adair |
| 5,325,746 A | 7/1994 | Anderson |
| 5,325,868 A | 7/1994 | Kimmelstiel |
| 5,329,942 A | 7/1994 | Gunther et al. |
| 5,330,466 A | 7/1994 | Imran |
| 5,330,482 A | 7/1994 | Gibbs et al. |
| 5,333,609 A | 8/1994 | Bedingham et al. |
| 5,334,148 A | 8/1994 | Martin |
| 5,336,191 A | 8/1994 | Davis et al. |
| 5,338,300 A | 8/1994 | Cox |
| 5,339,833 A | 8/1994 | Berthiaume et al. |
| 5,346,498 A | 9/1994 | Greelis et al. |
| 5,354,310 A | 10/1994 | Garnic et al. |
| 5,358,478 A | 10/1994 | Thompson et al. |
| 5,358,493 A | 10/1994 | Schweich, Jr. et al. |
| 5,358,496 A | 10/1994 | Ortiz et al. |
| 5,364,355 A | 11/1994 | Alden et al. |
| 5,365,943 A | 11/1994 | Jansen |
| 5,366,444 A | 11/1994 | Martin |
| 5,368,564 A | 11/1994 | Savage |
| 5,370,657 A | 12/1994 | Irie |
| 5,382,259 A | 1/1995 | Phelps et al. |
| 5,383,887 A | 1/1995 | Nadal |
| 5,383,892 A | 1/1995 | Cardon et al. |
| 5,383,923 A | 1/1995 | Webster, Jr. |
| 5,385,562 A | 1/1995 | Adams et al. |
| 5,396,897 A | 3/1995 | Jain et al. |
| 5,399,164 A | 3/1995 | Snoke et al. |
| 5,403,274 A | 4/1995 | Cannon |
| 5,403,324 A | 4/1995 | Ciervo et al. |
| 5,415,603 A | 5/1995 | Tuzuki et al. |
| 5,415,630 A | 5/1995 | Gory et al. |
| 5,417,684 A | 5/1995 | Jackson et al. |
| 5,421,348 A | 6/1995 | Larnard |
| 5,421,832 A | 6/1995 | Lefebvre |
| 5,423,331 A | 6/1995 | Wysham |
| 5,425,711 A | 6/1995 | Ressemann et al. |
| 5,443,081 A | 8/1995 | Klosterman |
| 5,456,667 A | 10/1995 | Ham et al. |
| 5,462,527 A | 10/1995 | Stevens-Wright et al. |
| 5,466,222 A | 11/1995 | Ressemann et al. |
| 5,466,225 A | 11/1995 | Davis et al. |
| 5,476,104 A | 12/1995 | Sheahon |
| 5,477,856 A | 12/1995 | Lundquist |
| 5,484,419 A | 1/1996 | Fleck |
| 5,487,392 A | 1/1996 | Haaga |
| 5,490,859 A | 2/1996 | Mische et al. |
| 5,507,769 A | 4/1996 | Marin et al. |
| 5,527,276 A | 6/1996 | Bruce |
| 5,545,136 A | 8/1996 | Berger |
| 5,549,553 A | 8/1996 | Ressemann et al. |
| 5,549,554 A | 8/1996 | Miraki |

| | | | | | | |
|---|---|---|---|---|---|---|
| 5,549,626 A | 8/1996 | Miller et al. | | 6,187,025 B1 * | 2/2001 | Machek ..................... 606/200 |
| 5,562,725 A | 10/1996 | Schmitt et al. | | 6,251,122 B1 * | 6/2001 | Tsukernik .................. 606/200 |
| 5,568,865 A | 10/1996 | Mase et al. | | 6,264,664 B1 | 7/2001 | Avellanet |
| 5,571,091 A | 11/1996 | Davis et al. | | 6,331,183 B1 * | 12/2001 | Suon ........................... 606/200 |
| 5,573,530 A | 11/1996 | Fleury et al. | | 6,342,062 B1 * | 1/2002 | Suon et al. .................. 606/200 |
| 5,595,185 A | 1/1997 | Erlich | | 6,447,530 B1 * | 9/2002 | Ostrovsky et al. ........... 606/200 |
| 5,603,722 A | 2/1997 | Phan et al. | | 6,537,294 B1 * | 3/2003 | Boyle et al. .................. 606/200 |
| 5,605,162 A | 2/1997 | Mirzaee et al. | | 2002/0026202 A1 | 2/2002 | Honey et al. |
| 5,641,067 A | 6/1997 | Ellis | | 2004/0078044 A1 | 4/2004 | Kear et al. |
| 5,642,736 A | 7/1997 | Avitall | | | | |
| 5,643,296 A | 7/1997 | Hundertmark et al. | | FOREIGN PATENT DOCUMENTS | | |
| 5,643,297 A | 7/1997 | Nordgren et al. | | EP | 0 277 366 | 8/1988 |
| 5,645,533 A | 7/1997 | Blaeser et al. | | EP | 0 427 429 A2 | 5/1991 |
| 5,658,296 A | 8/1997 | Bates et al. | | EP | 0 472 334 | 2/1992 |
| 5,662,671 A | 9/1997 | Barbut et al. | | EP | 0 533 511 A1 | 3/1993 |
| 5,665,092 A | 9/1997 | Mangiardi et al. | | EP | 0 293 605 B1 | 8/1993 |
| 5,666,968 A | 9/1997 | Imran et al. | | EP | 0 737 450 | 10/1996 |
| 5,667,488 A | 9/1997 | Lundquist et al. | | EP | 0 743 046 | 11/1996 |
| 5,669,933 A | 9/1997 | Simon et al. | | EP | 0 784 988 | 7/1997 |
| 5,695,519 A | 12/1997 | Summers et al. | | EP | 0 966 920 A2 | 12/1999 |
| 5,707,376 A | 1/1998 | Kavteladze et al. | | JP | 4 126 512 U | 11/1992 |
| 5,720,764 A | 2/1998 | Naderlinger | | JP | H05-116 U | 1/1993 |
| 5,728,133 A | 3/1998 | Kontos | | JP | 2002-125978 A | 5/2002 |
| 5,730,150 A | 3/1998 | Peppel et al. | | WO | WO 93/20876 | 10/1993 |
| 5,746,758 A | 5/1998 | Nordgren et al. | | WO | WO 94/16762 | 8/1994 |
| 5,769,816 A | 6/1998 | Barbut et al. | | WO | WO 96/01591 | 1/1996 |
| 5,779,716 A | 7/1998 | Cano et al. | | WO | WO 96/23542 | 8/1996 |
| 5,792,300 A | 8/1998 | Inderbitzen et al. | | WO | WO 97/20504 | 6/1997 |
| 5,795,308 A | 8/1998 | Russin | | WO | WO 97/27808 | 8/1997 |
| 5,795,322 A | 8/1998 | Boudewijn | | WO | WO 97/42879 | 11/1997 |
| 5,797,858 A | 8/1998 | Rourke | | WO | WO 98/08441 | 3/1998 |
| 5,797,952 A | 8/1998 | Klein | | WO | WO 98/23322 | 6/1998 |
| 5,800,409 A | 9/1998 | Bruce | | WO | WO 98/33443 | 8/1998 |
| 5,800,445 A | 9/1998 | Ratcliff et al. | | WO | WO 98/34673 | 8/1998 |
| 5,800,457 A | 9/1998 | Gelbfish | | WO | WO 98/36786 | 8/1998 |
| 5,800,525 A | 9/1998 | Bachinski et al. | | WO | WO 98/38920 | 9/1998 |
| 5,807,276 A | 9/1998 | Russin | | WO | WO 98/38929 | 9/1998 |
| 5,810,744 A | 9/1998 | Chu et al. | | WO | WO 98/39053 | 9/1998 |
| 5,810,835 A | 9/1998 | Ryan et al. | | WO | WO 98/46297 | 10/1998 |
| 5,810,849 A | 9/1998 | Kontos | | WO | WO 98/47447 | 10/1998 |
| 5,810,874 A | 9/1998 | Lefebvre | | WO | WO 98/50103 | 11/1998 |
| 5,814,064 A | 9/1998 | Daniel et al. | | WO | WO 98/51237 | 11/1998 |
| 5,817,102 A | 10/1998 | Johnson et al. | | WO | WO 98/55175 | 12/1998 |
| 5,827,312 A | 10/1998 | Brown et al. | | WO | WO 99/04704 | 2/1999 |
| 5,827,324 A | 10/1998 | Cassell et al. | | WO | WO 99/09895 | 3/1999 |
| 5,833,644 A | 11/1998 | Zadno-Azizi et al. | | WO | WO 99/23976 | 5/1999 |
| 5,833,650 A | 11/1998 | Imran | | WO | WO 99/44506 | 9/1999 |
| 5,846,260 A | 12/1998 | Maahs | | WO | WO 00/12009 | 3/2000 |
| 5,848,964 A | 12/1998 | Samuels | | WO | WO 00/12010 | 3/2000 |
| 5,855,567 A | 1/1999 | Reesemann | | WO | WO 01/05311 | 1/2001 |
| 5,855,585 A | 1/1999 | Kontos | | | | |
| 5,860,953 A | 1/1999 | Snoke et al. | | * cited by examiner | | |

ERCP CATHETER WITH A REMOVABLE HANDLE FOR LITHOTRIPTOR COMPATIBLE BASKET

This application claims priority to U.S. Provisional Application Ser. No. 60/403,123 filed Aug. 13, 2002.

BACKGROUND OF THE INVENTION

The present invention relates generally to new and useful improvements in a removable handle for a medical device and more particularly to an ERCP catheter with a removable handle for a lithotriptor compatible basket.

Endoscopic retrogradecholangiopancreatography (ERCP) enables the physician to diagnose problems in the liver, gallbladder, bile ducts and pancreas. ERCP is used primarily to diagnose and treat conditions such as blockage of the bile ducts by gallstones and blockage of the pancreatic ducts from stones. ERCP combines the use of x-rays and an endoscope. The physician can see the inside of stomach and duodenum and inject dyes into the ducts in the biliary tree and pancreas through the endoscope so that the organs can be visualized on x-rays. Once a stone is visualized the physician can insert instruments into the scope to remove the stone. One such instrument is an ERCP catheter having a drive cable and basket assembly inserted within the catheter. Conventionally, to facilitate stone removal, a sphincterotomy is performed on the papilla to ensure that the opening of the bile duct is as large as possible. An ERCP catheter is introduced through the endoscopy channel and the basket assembly captures the stone using a conventional method. In certain circumstances, it may become evident that the stone is too large to be removed in one piece despite the sphincterotomy. At this point, the drive cable is tensioned such that the basket holding the stone is wedged against the papilla to retain the captured stone. Next, the ERCP catheter and basket drive cable is cut so that the catheter can be removed over the drive cable leaving the basket and stone in place. Subsequently, a lithotriptor, such as the Wilson-Cook® Conquest TTC™ Lithotriptor or the Wilson-Cook® Soehendra®, is used to crush the stone into smaller fragments.

One disadvantage with such conventional ERCP catheters is the need to cut a portion of the ERCP catheter and the drive cable to remove the catheter and feed a through-the-scope lithotriptor over the drive cable to crush the stone.

Another disadvantage is once the drive cable has been cut, the overall length of the drive cable is shortened considerably making it more difficult for the operator to manipulate the drive cable and retain captured stone.

Further, the drive cable is typically made up of several multi-filament cables which are intertwined. Once the drive cable has been cut, the distal ends of the multi-filament cables tend to fray adding to the difficulty of handling the drive cable, retaining the stone and using the through-the-scope lithotriptor to crush the stone.

These problems are overcome through the use of catheter with a removable handle constructed in accordance with this invention.

SUMMARY OF THE INVENTION

The present invention is directed to a method and device for the endoscopic removal of biliary stones and foreign bodies. The present invention includes an ERCP catheter with a removable handle for a lithotriptor compatible basket.

In one preferred embodiment, the ERCP catheter with removable handle for a lithotriptor compatible basket comprises a multi-lumen ERCP catheter, a multi-port connector attached to the catheter, and a removable handle assembly attached to the multi-port connector. Preferably, the catheter comprises a catheter wire guide lumen and a catheter drive cable lumen. The multi-port connector comprises a connector drive cable lumen axially aligned with the catheter drive cable lumen, a connector wire guide lumen axially aligned with the catheter wire guide lumen, and a wire guide port in fluid communication with the connector wire guide lumen. Preferably, the multi-port connector further includes an injection port in fluid communication with the connector wire guide lumen. A wire guide extends through the catheter wire guide lumen, the connector wire guide lumen and exits the wire guide port.

The removable handle assembly comprises a handle lumen which is axially aligned with the connector drive cable lumen, a control handle member slidably and detachably associated with a gripping handle member, a tightening mechanism for releasably affixing the axial position of the drive cable relative to the control handle member such that axial movement of the control handle member drives the drive cable and actuates the basket assembly, and a detachable cable loop for storing a portion of the drive cable. A drive cable extends through the catheter drive cable lumen, the connector drive cable lumen, the removable handle assembly and into the cable loop. A basket assembly is formed at the distal end of the drive cable and can be expanded and collapsed as it is moved in and out of the catheter. Preferably, the drive cable includes a coating along at least a portion of the drive cable to provide support.

In an alternate preferred embodiment, the ERCP catheter with removable handle for a lithotriptor compatible basket comprises a single-lumen, ERCP catheter comprising a drive cable lumen, a removable handle assembly comprising a handle lumen axially aligned with the catheter drive cable lumen and a connector interconnecting the single-lumen ERCP catheter and the removable handle assembly. The connector comprises a connector drive cable lumen axially aligned with the catheter drive cable lumen. Preferably, the connector further comprises an injection port. A drive cable extends through the drive cable lumen, the connector drive cable lumen, and into the removable handle assembly. Preferably, the drive cable includes a coating along at least a portion of the drive cable to provide support. A basket assembly is formed at the distal end of the drive cable and can be expanded and collapsed as it is moved in and out of the catheter. The removable handle further comprises a control handle member slidably and detachably associated with a gripping handle member. The control handle member further comprises a tightening mechanism for releasably affixing the axial position of the drive cable relative to the control handle member such that axial movement of the control handle member drives the drive cable and actuates the basket assembly and a detachable cable loop for storing a portion of the drive cable.

DETAILED DESCRIPTION OF THE INVENTION

FIGS. 1-10 show a device 10 according to one preferred embodiment of the invention. The ERCP catheter with removable handle for a lithotriptor compatible basket 10 of the present invention comprises a catheter 20 and a multi-port connector 50 attached to the catheter 20 and a removable handle assembly 70 attached to the multi-port connector 50. Preferably, the catheter 20 is a multi-lumen ERCP catheter comprising a wire guide 60 disposed within a catheter wire guide lumen 22 and a drive cable 30 disposed within a catheter drive cable lumen 24. Preferably, the multi-port connector 50 comprises a wire guide port 61, a connector wire guide lumen 52 and a connector drive cable lumen 54. The removable handle assembly 70 comprises a handle lumen which is axially aligned with the connector drive cable lumen 54 and the catheter drive cable lumen 24. The drive cable 30 extends through the catheter drive cable lumen 24, the connector drive cable lumen 54 and into the removable handle assembly 70. A wire guide 60 extends through the catheter wire guide lumen 22, the connector wire guide lumen and exits the wire guide port 61.

Figure 1:
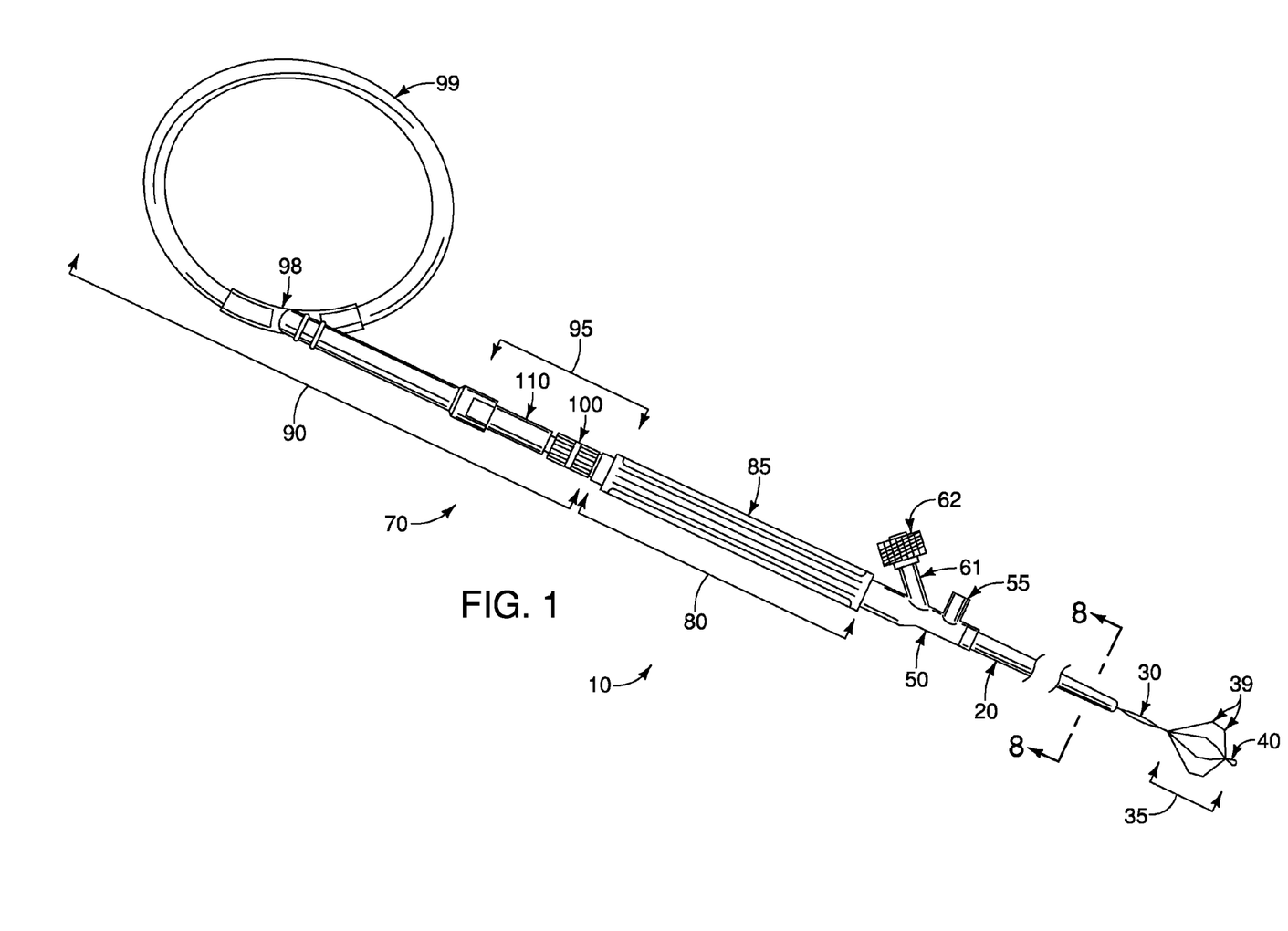
FIGS. 1 and 3 are perspective views of one embodiment of a device according to the present invention, showing the basket assembly extended relative to the catheter.
Figure 2:
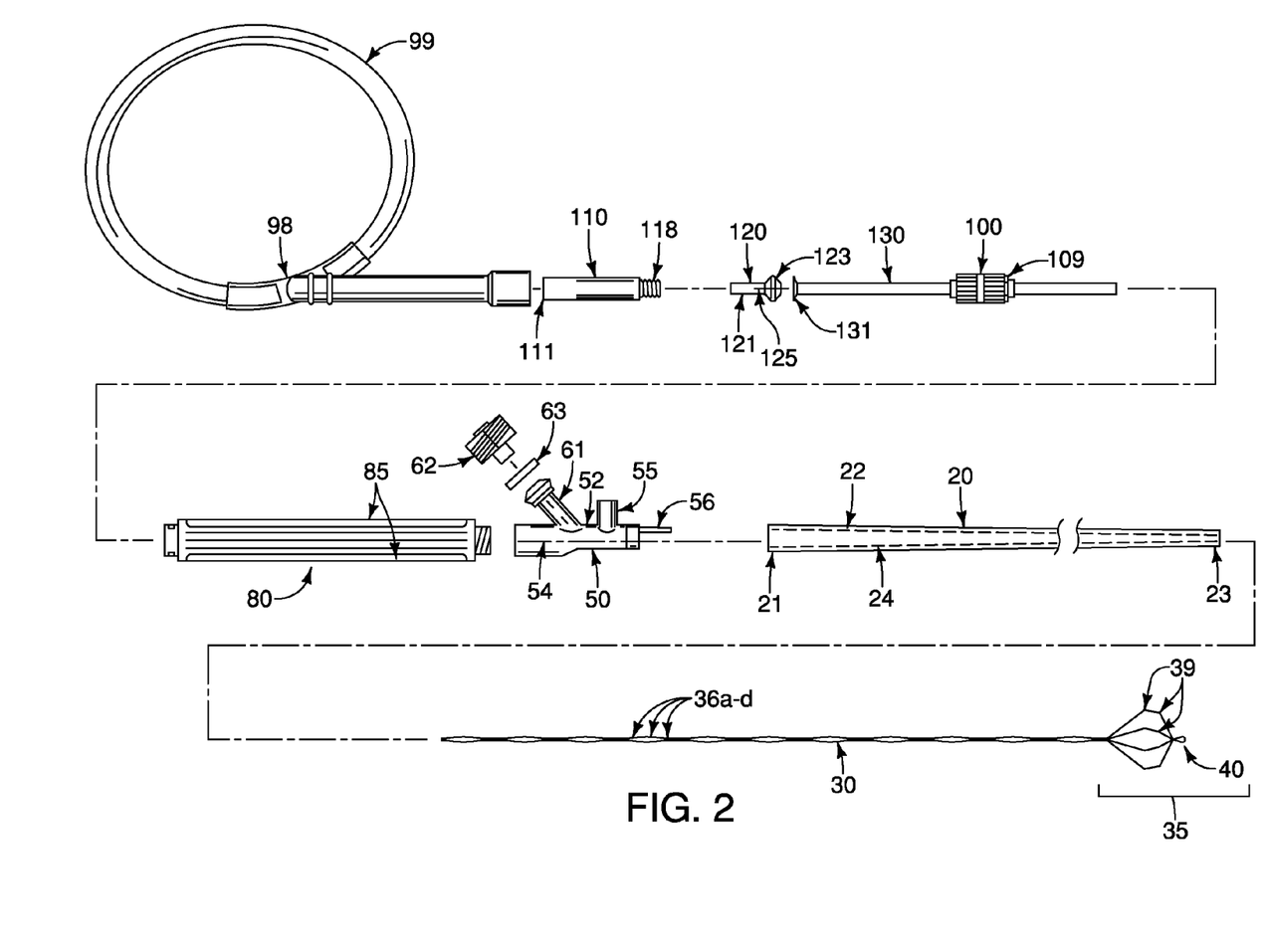
FIG. 2 is an exploded perspective view of the device shown in FIGS. 1 and 3.
Figure 3:
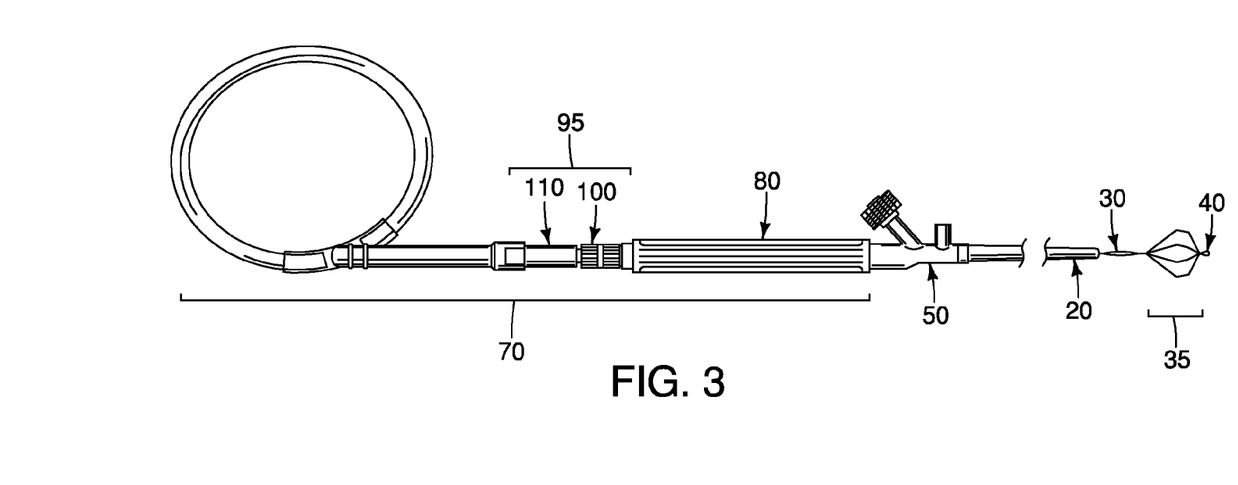

Referring to FIGS. 1-2, ERCP catheters are intended for advancement through the accessory channel of endoscope into a body passage such as the gastrointestinal system. It is contemplated, therefore, that the ERCP catheter 20 of the present invention may have any size that fits within the accessory channel of an endoscope. Preferably, the catheter 20 comprises a proximal end 21 having a proximal diameter and a distal end 23 having a distal diameter. More preferably, the catheter 20 tapers from a larger proximal diameter to a smaller distal diameter. Preferably, for the current industry standard sized endoscope, the proximal diameter can range in size up to about 20 French ("Fr.") and the distal diameter can range in size up to about 13 Fr. More preferably, the proximal diameter can range in size from about 7 Fr. to about 16 Fr. and the distal diameter can range in size from about 3 Fr. to about 11 Fr. Most preferably, the proximal diameter end is about 12 Fr and the distal diameter end is about 8 Fr.

Preferably, the catheter 20 is a flexible tube of conventional construction. By way of example, and not by way of limitation, catheter 20 may be an extrusion of any suitable material such as (irradiated) polyethylene, nylon or tetrafluoroethylene. Catheter 20 may also be extruded from polyurethane. Multi-lumen ERCP catheters have two or more independent lumens extending continuously to ports at the distal end for injection of a contrast medium simultaneously with a wire guide for ERCP procedures and for the passage of stone baskets for catheterization, diagnosis and treatment within the biliary or pancreatic duct systems.

Figures 7, 8:
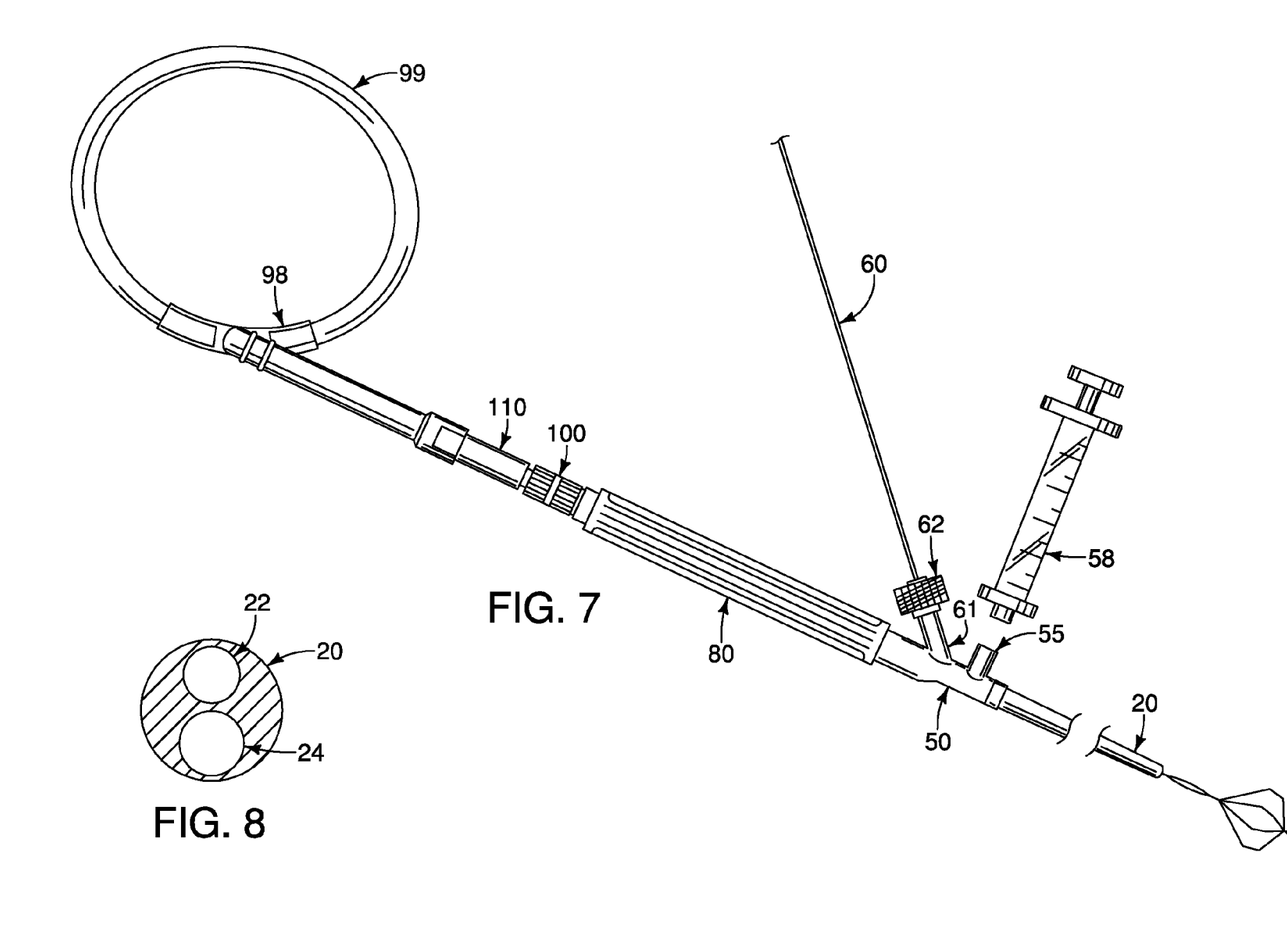
FIG. 7 is a side view of the device shown in FIGS. 1 and 3, showing the wire guide extending from the wire guide port and a syringe relative to the injection port.
FIG. 8 is a sectional view taken along line 8-8 of FIG. 1.

Referring to FIGS. 1-2 and 8, the ERCP catheter with a removable handle for lithotriptor compatible basket 10 of the present invention includes a catheter wire guide lumen 22 and a catheter drive cable lumen 24. The catheter wire guide lumen 22 may be the same size or smaller than catheter drive cable lumen 24. Preferably, the catheter wire guide lumen 22 and the catheter drive cable lumen 24 taper from the catheter proximal end 21 to the catheter distal end 23. More preferably, the catheter wire guide lumen 22 and the catheter drive cable lumen 24 are elliptical in shape. Most preferably, the catheter wire guide lumen 22 is smaller than the catheter drive cable lumen 24 as shown in FIG. 8. However, other shapes including, but not limited to, round, oval, elliptical or hemispherical may be used.

Figure 9:
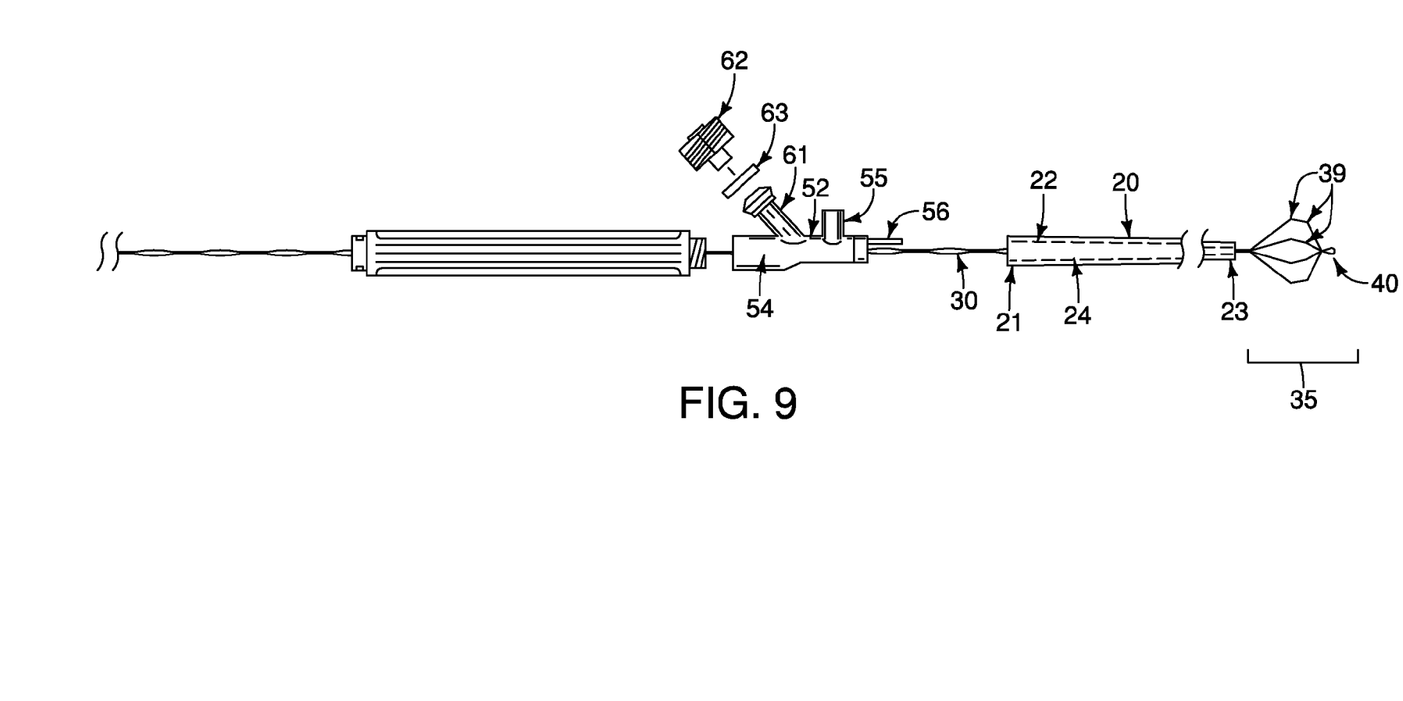
FIG. 9 is an exploded partial view of the device shown in FIGS. 1 and 3.

Referring to FIGS. 1-2 and 9, the drive cable 30 comprises a plurality of resilient wires 36 intertwined, each of the plurality of resilient wires 36 comprising smaller, intertwined, multi-filament wires. A basket assembly 35 is formed at the distal end of the drive cable. Preferably, drive cable 30 comprises at least four cables 36a-d intertwined. Preferably, the drive cable 30 has an overall length of about 300 cm to about 400 cm. Most preferably, the drive cable 30 has an overall length of about 350 cm.

Figure 11:
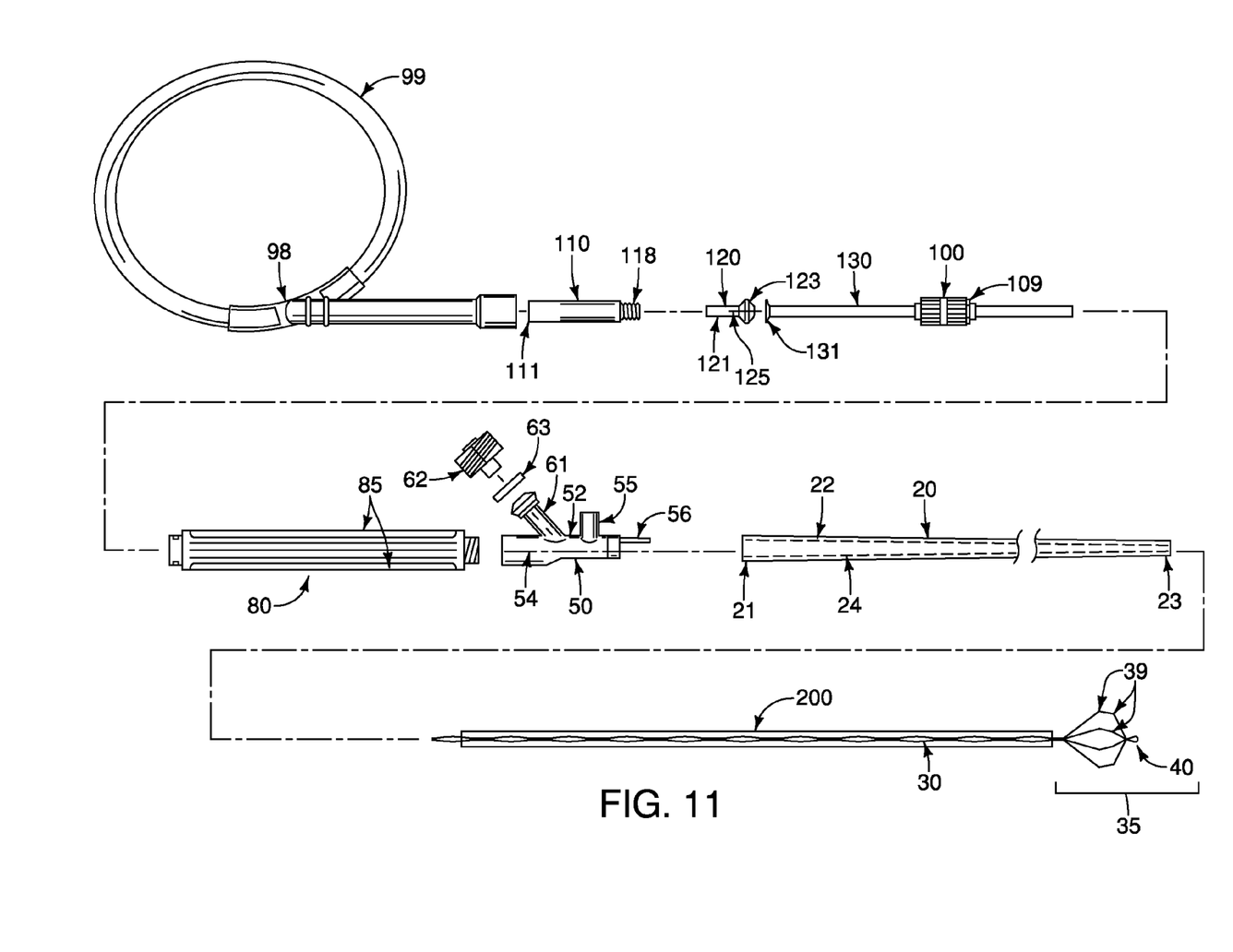
FIG. 11 is an exploded perspective view of an alternate preferred embodiment of a device according to the present invention.

Referring to FIG. 11, drive cable 30 further comprises a coating 200 along at least a portion of the drive cable 30 length. Coating 200 prevents the drive cable 30 from bunching in catheter 20 as catheter 20 is contorted within the body passage of a patient. Any coating capable of providing support to the drive cable is contemplated including, but not limited to, polytetrafluoroethylene (PTFE), polyolefin, polyvinyl chloride (PVC), polyester (PET) and fluorinated ethylene propylene (FEP). The coating can be applied by any method known in the art including, but not limited to, the use of heat-shrink tubing, dip coating, spraying or extrusion. Non-limiting examples of suitable heat-shrink tubing materials include PTFE, polyolefin, PVC, PET and FEP. PTFE is also a non-limiting example of a suitable spray material. Suitable dip coating materials include hydrophilic, highly lubricious coatings and any coating that reduces the friction within the handle and provides column strength to the drive cable.

Preferably, coating 200 extends along the distal end of drive cable 30 proximal to the basket assembly 35 and has a length of about 150 cm to about 200 cm. More preferably, coating 200 has a length of about 175 cm to about 200 cm. Most preferably, the coating 200 has a length of about 200 cm.

A basket assembly 35 is formed by securing the plurality of resilient wires 36 by proximal and distal cannula. A plurality of bends 39 is formed in each of the resilient wires 36 so as to define a basket when these wires are expanded. The distal cannula has a rounded extremity, or ball tip, 40, which prevents the basket assembly 35 from retracting completely into the catheter 20.

Figure 5:
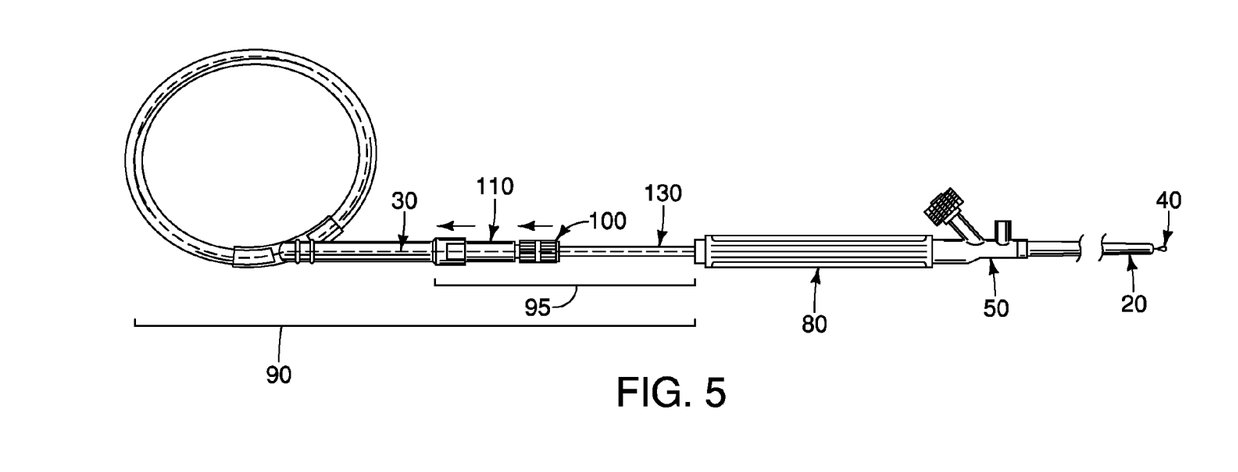
FIG. 5 is a perspective view of the device shown in FIGS. 1 and 3, showing the drive cable loop retaining a portion of the drive cable and the control handle member and the basket assembly fully retracted relative to the catheter.
Figure 6:
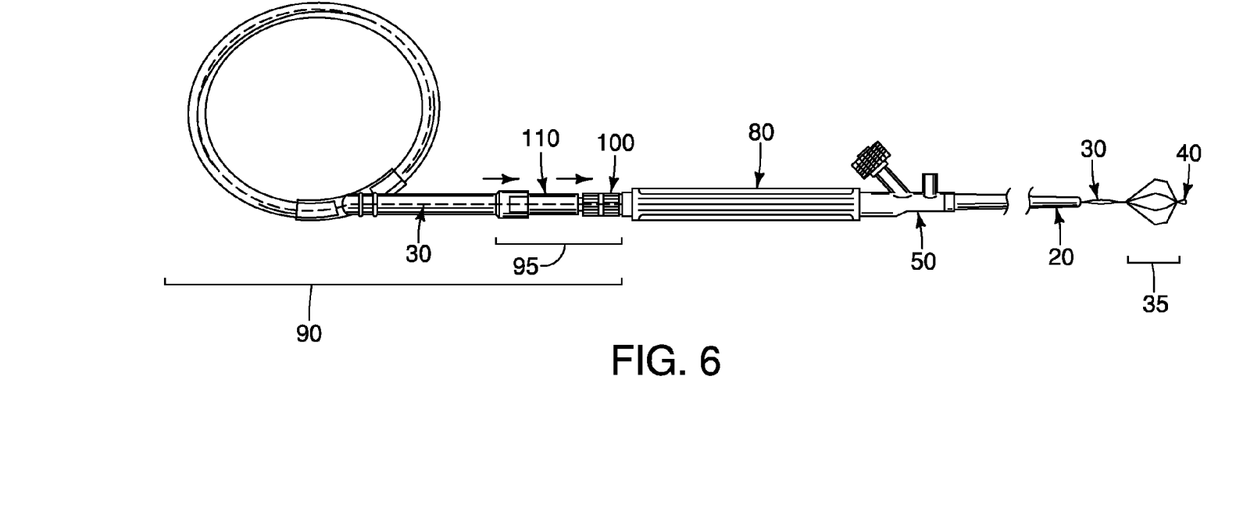
FIG. 6 is a perspective view of the device shown in FIG. 1 showing the drive cable loop retaining a portion of the drive cable and the control handle member and the basket assembly fully extended relative to the catheter.

As shown in FIGS. 2 and 9, the drive cable 30 is passed through catheter drive cable lumen 24 of FIG. 8. Referring to FIGS. 5 and 6, the drive cable 30 can be driven proximally and distally to move the basket assembly 35 past the catheter distal end 23. As the basket assembly 35 moves past the catheter distal end 23, the basket assembly 35 can be resiliently expanded or collapsed in a direction perpendicular to the axis of the catheter drive cable lumen 24.

As shown in FIGS. 2 and 9, a connector 50 is attached to the catheter 20. Preferably, the connection between connector 50 and catheter 20 is an interference fit. In one preferred embodiment, connector 50 is a multi-port connector comprising a wire guide port 61, an injection port 55, a connector wire guide lumen 52 and a connector drive cable lumen 54. The connector wire guide lumen 52 is axially aligned with catheter wire guide lumen 22 and the connector drive cable lumen 54 is axially aligned with catheter drive cable lumen 24. Preferably, the multi-port connector 50 also includes a connector support cannula 56, which extends from connector wire guide lumen 52 and forms an interference fit with catheter wire guide lumen 22.

Referring to FIGS. 2, 7 and 9, the wire guide port 61 and injection port 55 are in fluid communication with the connector wire guide lumen 52. The injection port 55 preferably includes a luer lock to which a syringe 58 may be secured as shown in FIG. 7. Preferably, the wire guide port 61 includes an O-ring cap 62 and a sealing O-ring 63. The wire guide 60 extends through the catheter wire guide lumen 22, the connector wire guide lumen 52 and exits wire guide port 61 through the O-ring cap 62. The O-ring cap 62 may be tightened such that the sealing O-ring 63 is compressed to form a seal around wire guide 60 to prevent fluid injected through injection port 55 from escaping through wire guide port 61.

Referring to FIGS. 1-2, the removable handle assembly 70 is attached to connector 50 and includes a gripping handle member 80 and a control handle member 90 and a handle lumen therebetween. The gripping handle member 80 and the control handle member 90 are slidably and detachably associated with one another as shown in FIGS. 5-6. As shown in FIGS. 1-2, the gripping handle member 80 is connected to the multi-port connector 50. The handle lumen extends through the gripping handle member 80 and is axially aligned with connector drive cable lumen 54. In a preferred embodiment, the gripping handle member 80 further comprises gripping elements 85.

Referring to FIGS. 1-2 and 5-6, the control handle member 90 comprises a tightening mechanism 95 and a cable loop 99 for storing a portion of the drive cable 30. The handle lumen extends through the control handle member 90 and into the cable loop 99. As shown in FIGS. 1-2, the tightening mechanism 95 is axially aligned with the connector drive cable lumen 54 and the catheter drive cable lumen 24. The drive cable 30 extends through catheter drive cable lumen 24, the connector drive cable lumen 54 through the handle lumen, the tightening mechanism 95 and into the cable loop 99.

The tightening mechanism 95 has a closed, or tightened, position and an opened, or loosened, position. In the tightened position, the tightening mechanism 95 grips the drive cable 30 such that axial movement of the control handle member 90 moves the drive cable 30 proximally and distally relative to the catheter 20. During such movement, the basket assembly moves past the catheter distal end 23 and the basket assembly 35 can be resiliently expanded or collapsed in a direction perpendicular to the axis of the drive cable 30. As shown in FIGS. 5-6, pulling the control handle member 90 proximally causes the drive cable 30 and basket assembly 35 to retract relative to the catheter 20. In its fully retracted position, the basket assembly 35 is collapsed and retracted within the catheter 20 such that only the ball tip 40 prevents the basket assembly 35 from retracting completely past the catheter distal end 23. Similarly, pushing the control handle member 90 distally causes the drive cable 30 and basket assembly 35 to extend relative to the catheter 20. In its fully extended position, the control handle member 90 abuts the gripping handle member 80 and the basket assembly 35 is fully extended relative to the catheter 20 and fully expanded as shown in FIG. 6.

In the loosened position, the tightening mechanism 95 releases the drive cable 30 and permits the drive cable 30 and basket assembly 35 to be freely moveable independent of the catheter 20. Also, in the loosened position the physician may remove the entire catheter 20 and handle assembly 70 from over the drive cable 30, leaving the drive cable 30 within the duct, as well as the wire guide 60 if so desired.

Referring to FIG. 2, in one preferred embodiment, the tightening mechanism 95 comprises a luer lock type connection. More specifically, the tightening mechanism 95 includes a male luer lock adapter (MLLA) 100, a pin vise 110, a collet 120 and a support member 130. The MLLA 100 includes a longitudinal bore, a cylindrical outer wall having a gripping surface thereon, internal threads and a protrusion 109. The protrusion 109 slidably engages the gripping handle member 80.

The support member 130 passes through the longitudinal bore of the MLLA 100 and provides support for the drive cable 30 as the control member handle 90 is pulled proximally and pushed distally to retract and extend the drive cable 30 and to collapse and expand the basket assembly 35. The support member 130 comprises a cannula and preferably includes a flared proximal end 131.

The pin vise 110 includes a longitudinal bore, a cylindrical outer wall having a gripping surface thereon, and external threads 118 for threadably engaging the internal threads of the MLLA 100.

The collet 120 grips the wires 36 that comprise the drive cable 30 of the basket assembly 35 allowing the control handle member 90 to actuate the drive cable 30 to open and close the basket assembly 35. The collet 120 is disposed in part within pin vise 110 and in part within MLLA 100. Preferably, the collet 120 comprises a cylindrical portion 121, a distal head portion 123 and at least one longitudinal slot 125. Preferably, collet 120 includes two longitudinal slots 125 which divide collet distal head portion 123 and a portion of collet cylindrical portion 121 into four quarter sections. More preferably, the collet cylindrical portion 121 is received within the pin vise 110 and the collet distal head portion 123 extends from the pin vise 110 and abuts the support member flared proximal end 131 and is received within the MLLA 100.

Figure 10:
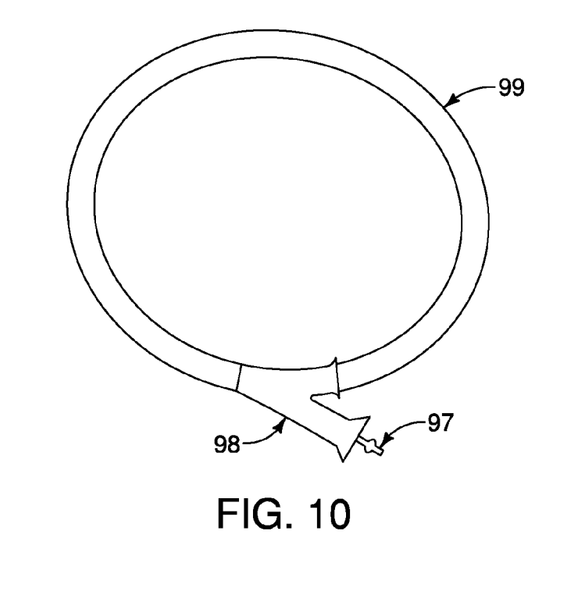
FIG. 10 is a perspective view of an alternate preferred embodiment of the cable loop of the present invention.

Referring to FIGS. 2 and 10, the cable loop 99 is attached to the control handle member 90 and, preferably, is detachably connected to the pin vise 110. More preferably, the connection between the cable loop 99 and the pin vise 110 is a snap-fit connection. The cable loop 99 has a diameter between about 5 to about 7 inches, more preferably about 6 inches. Cable loop 99 may be constructed of polyethylene tubing and a polyethylene Y-fitting 98 as shown in FIGS. 1-7. More preferably the Y-fitting 98 is molded of a rigid plastic, e.g., polyvinyl chloride (PVC) and includes a protrusion 97 as shown in FIG. 10. The protrusion 97 forms a snap-fit connection with the pin vise 110. Alternatively, the cable loop 99 may be molded of a rigid plastic. Cable loop 99 retains a portion of drive cable 30. Preferably, cable loop 99 retains about 140 to about 150 cm of drive cable.

Figure 4:
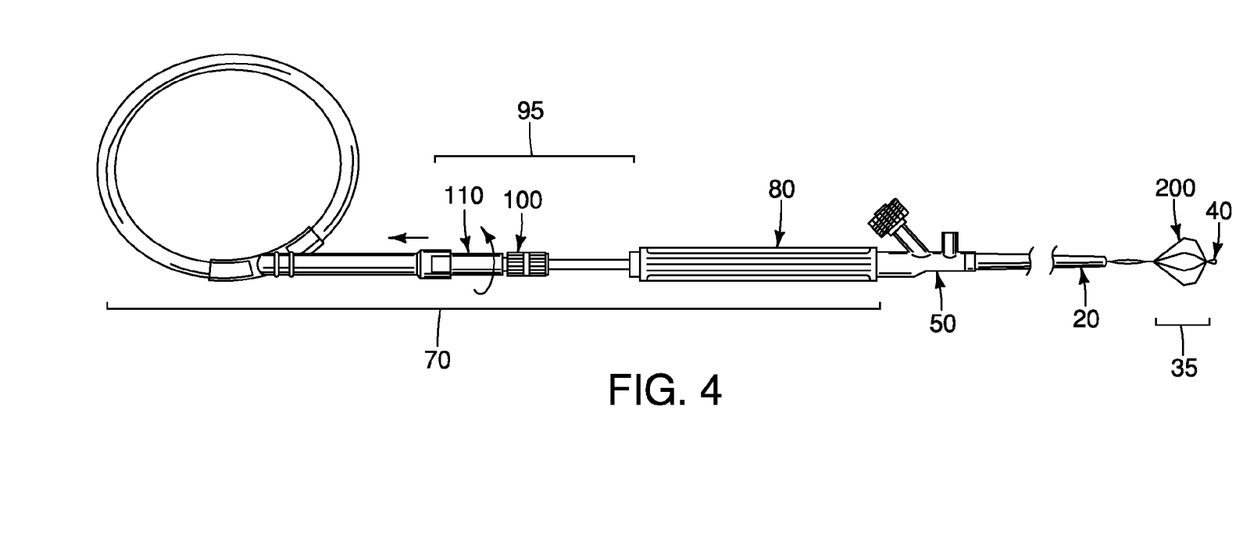
FIG. 4 is a perspective view of the device shown in FIGS. 1 and 3, showing the removable handle pulled proximally to retract the basket assembly with the captured stone relative to the catheter and showing the rotation of pin vise relative to the male luer lock adapter to loosen the tightening mechanism.

Referring to FIG. 4, rotational movement of pin vise 110 relative to the MLLA 100 tightens and loosens the tightening mechanism 95. In the tightened configuration, the pin vise 110 and the MLLA 100 are threaded together and the MLLA internal threads tighten about the pin vise external threads 118 to compress the collet 120. As the collet is compressed, it grips the drive cable 30. This allows the control handle member 90 to move the drive cable 30 relative to the catheter 20 to open and close the basket assembly 35 as shown in FIGS. 5 and 6.

Conversely, in the loosened configuration, the MLLA internal threads release the external threads 118 of the pin vise 110 and the collet 120 releases the drive cable 30. In this configuration, the control handle member 90 is unable to actuate the drive cable 30 and basket assembly 35, causing the drive cable 30 and basket assembly 35 to be freely moveable independent of the catheter 20.

The ERCP catheter with a removable handle for lithotriptor compatible basket of the present invention is operated as follows. A physician inserts an endoscope down the patient's throat, locates the papilla of vater, and views the bile or pancreatic duct. Then, the physician inserts a conventional ERCP catheter with a wire guide 60 into the endoscope accessory channel and enters the papilla. The physician gains access to the duct by pushing the wire guide 60 into the duct and advances the wire guide 60 to the stone. The conventional ERCP catheter is removed leaving the wire guide 60 within the endoscope in position within the duct at the target location. Next, the physician feeds the proximal end of the wire guide 60 into the wire guide lumen 22 of the multi-lumen ERCP catheter with removable handle for a lithotriptor compatible basket of the present invention with the tightening mechanism 95 in the tightened configuration and the basket assembly 35 retraced as shown in FIG. 5 and inserts it into the accessory channel of the endoscope. The multi-lumen ERCP catheter with removable handle for a lithotriptor compatible basket of the present invention is advanced along the wire guide 60 to the target location, and the physician may, if desired, choose to subsequently remove the wire guide 60.

Alternatively, if the patient has previously undergone a sphincterotomy on the papilla to enlarge the opening of the duct, an endoscope pre-loaded with a single-lumen ERCP catheter with removable handle for a lithotriptor compatible basket of the present invention is inserted directly into the papilla and the stone is visualized under fluoroscopy. Under this approach, the enlarged papilla eliminates the need of the wire guide 60 to gain access to the stone within the duct. Instead, the endoscope with the preloaded single-lumen ERCP catheter with removable handle for a lithotriptor compatible basket is advanced directly to the stone.

Under either procedure, the basket assembly 35 is first advanced and then retracted to capture the stone under endoscopy. As shown in FIGS. 5-6, pulling the control handle member 90 proximally causes the drive cable 30 and the basket assembly 35 to retract relative to the catheter 20. During such movement, the basket assembly 35 moves past the catheter distal end 23 and the basket assembly 35 collapses in a direction perpendicular to the axis of the drive cable 30. In its fully retracted position, the basket assembly 35 is collapsed and retracted within the catheter 20. The ball tip 40 prevents the basket assembly 35 from completely retracting past the catheter distal end 23 as shown in FIG. 5. Similarly, pushing the control handle member 90 distally causes the drive cable 30 and basket assembly 35 to extend relative to the catheter 20. During such movement, the basket assembly 35 moves past the catheter 20 and expands in a direction perpendicular to the axis of the drive cable 30. In its fully extended position, the control handle member 90 abuts the gripping handle member 80 and the basket assembly 35 is fully extended relative to the catheter 20 and fully expanded as shown in FIG. 6. The physician captures the stone by extending and retracting the basket assembly 35 in this manner.

If the captured stone is too large to be removed in one piece, the physician may remove the catheter 20 and handle assembly 70 and may use a through-the-scope lithotriptor, such as the Wilson-Cook® Conquest TTC™ Lithotriptor, or a lithotriptor cable and handle which is not used through the endoscope, such as the Wilson-Cook® Soehendra®, to crush the stone. As shown in FIG. 4, to remove the catheter 20 and handle assembly 70 while holding the captured stone 200, the physician unscrews the MLLA 100 and pin vise 110. When the tightening mechanism 95 is loosened, the collet 120 releases the drive cable 30 and the handle assembly 70 and catheter 20 can be removed over the drive cable 30. Alternatively, the cable loop 99 can be detached from the pin vise 110 to expose the drive cable 30. Then, the catheter 20 is removed by unscrewing the MLLA 100 and pin vise 110. In either approach, the physician and/or assistant can grip the drive cable 30 and maintain tension on the drive cable 30 and the captured stone as the catheter 20 is removed.

Once the catheter 20 is removed, the lithotriptor is fed onto and then connected to the drive cable 30. The exposed drive cable 30 enables the physician and/or assistant to grip the drive cable 30 on either side of the lithotriptor, and thus increases the ability to maintain the drive cable 30 and basket assembly 35 with the captured stone against the papilla to prevent the captured stone from escaping and sliding back into the duct. The sheath of the lithotriptor is more rigid than the catheter, allowing the sheath to provide more mechanical assistance in crushing the stone, which is accomplished by manipulating the lithotriptor handle.

Since the handle assembly 70 and catheter 20 are removable, it is no longer necessary to cut a portion of the catheter 20 and drive cable 30 to feed use a lithotriptor to crush the stone. Also, since the drive cable 30 is not cut and the wires 36 making up the drive cable 30 do not fray, the process of feeding the lithotriptor onto the drive cable 30 is also facilitated. Furthermore, the portion of the drive cable 30 stored in the cable loop 99 facilitates stone retention while the lithotriptor is positioned in place.

It should be appreciated that the present invention is capable of being incorporated in the form of a variety of embodiments, only a few of which have been illustrated and described.

The invention claimed is:

1. A method of removing a stone from a duct of a patient comprising the steps of:
   providing an apparatus comprising:
   a catheter;
   a connector attached to the catheter; and
   a removable handle assembly attached to the connector;
   a drive cable having a proximal end, a distal end and a basket assembly formed at the drive cable distal end and a coating along at least a portion of the drive cable proximal the basket assembly;
   wherein the catheter further comprises a catheter drive cable lumen,
   wherein the connector further comprises a connector drive cable lumen axially aligned with the catheter drive cable lumen and an injection port;
   wherein the removable handle assembly comprises a handle lumen axially aligned with the connector drive cable lumen, a control handle member slidably and detachably associated with a gripping handle member, a tightening mechanism and a detachable cable loop;
   wherein the drive cable extends through the catheter drive cable lumen, the connector drive cable lumen, the handle lumen, the control handle member, the gripping handle member, the tightening mechanism and into the detachable cable loop;

wherein the tightening mechanism releasably affixes the axial position of the drive cable relative to the control handle member such that axial movement of the control handle member relative to the gripping handle member drives the drive cable and causes the basket assembly to expand and collapse as the basket assembly moves into and out of the catheter;

tightening the tightening mechanism to affix the axial position of the drive cable relative to the control handle member;

pulling the control handle member proximally such that the basket assembly is collapsed and retracted within the catheter;

inserting the catheter to the proximity of the stone;

pushing the control handle member distally so as to extend and expand the basket assembly relative to the catheter and pulling the control handle member proximally so as to retract and collapse the basket assembly relative to the catheter to thereby capture the stone;

at least partially retracting the catheter from the duct and determining that the stone is too large to remove from the duct in one piece;

loosening the tightening mechanism and removing the catheter over the drive cable; and feeding a lithotriptor over the drive cable to crush the stone.

2. A method of removing a stone from a duct of a patient comprising the steps of:

providing an apparatus comprising:
  a catheter;
  a connector attached to the catheter; and
  a removable handle assembly attached to the connector;
  a drive cable having a proximal end, a distal end and a basket assembly formed at the drive cable distal end and a coating along at least a portion of the drive cable proximal the basket assembly;
  wherein the catheter further comprises a catheter drive cable lumen,
  wherein the connector further comprises a connector drive cable lumen axially aligned with the catheter drive cable lumen and an injection port;
  wherein the removable handle assembly comprises a handle lumen axially aligned with the connector drive cable lumen, a control handle member slidably and detachably associated with a gripping handle member, a tightening mechanism and a detachable cable loop;
  wherein the drive cable extends through the catheter drive cable lumen, the connector drive cable lumen, the handle lumen, the control handle member, the gripping handle member, the tightening mechanism and into the detachable cable loop;
  wherein the tightening mechanism releasably affixes the axial position of the drive cable relative to the control handle member such that axial movement of the control handle member relative to the gripping handle member drives the drive cable and causes the basket assembly to expand and collapse as the basket assembly moves into and out of the catheter;

tightening the tightening mechanism to affix the axial position of the drive cable relative to the control handle member;

pulling the control handle member proximally such that the basket assembly is collapsed and retracted within the catheter; inserting the catheter to the proximity of the stone; pushing the control handle member distally so as to extend and expand the basket assembly relative to the catheter and pulling the control handle member proximally so as to retract and collapse the basket assembly relative to the catheter to thereby capture the stone;

at least partially retracting the catheter from the duct and determining that the stone is too large to remove from the duct in one piece;

detaching the cable loop;

loosening the tightening mechanism and removing the catheter over the drive cable; and feeding a lithotriptor over the drive cable to crush the stone.

3. A method of removing a stone from a duct of a patient comprising the steps of:

providing an apparatus comprising:
  a catheter;
  a connector attached to the catheter;
  a removable handle assembly attached to the connector; and
  a drive cable comprising a basket assembly formed at a drive cable distal end, at least a portion of the drive cable extending through the catheter, the connector and the handle assembly;
  wherein the handle assembly is configured for removal from the apparatus over the drive cable without cutting the drive cable;

pulling a portion of the handle assembly proximally such that the basket assembly is collapsed and retracted within the catheter;

inserting the catheter to the proximity of the stone;

pushing the portion of the handle assembly distally so as to extend and expand the basket assembly relative to the catheter and pulling the portion of the handle assembly proximally so as to retract and collapse the basket assembly relative to the catheter to thereby capture the stone;

at least partially retracting the catheter from the duct and determining that the stone is too large to remove from the duct in one piece;

loosening the handle assembly and removing the handle assembly over the drive cable; and feeding a lithotriptor over the drive cable to crush the stone.

4. The method of claim 3, further comprising detaching a cable loop from the handle assembly.

5. The method of claim 3 further comprising removing the catheter over the drive cable.

* * * * *